United States Patent [19]

Rasberger et al.

[11] Patent Number: 5,665,273
[45] Date of Patent: Sep. 9, 1997

[54] HALS PHOSPHONITES AS STABILIZERS

[75] Inventors: Michael Rasberger, Riehen; Rita Pitteloud, Praroman, both of Switzerland

[73] Assignee: Ciba-Geigy Corporation, Tarrytown, N.Y.

[21] Appl. No.: 416,660

[22] Filed: Apr. 5, 1995

[30] Foreign Application Priority Data

Apr. 13, 1994 [CH] Switzerland .................. 1111/94

[51] Int. Cl.$^6$ .................. C09K 15/00; C07F 9/28
[52] U.S. Cl. .................. 252/397; 252/400.21; 524/99; 524/102; 546/22
[58] Field of Search .................. 252/400.21, 397; 524/99, 102; 546/22

[56] References Cited

U.S. PATENT DOCUMENTS

| | | | |
|---|---|---|---|
| 4,233,412 | 11/1980 | Rody et al. | 525/167 |
| 4,325,863 | 4/1982 | Hinsken et al. | 624/111 |
| 4,338,244 | 7/1982 | Hinsken et al. | 524/109 |
| 4,434,109 | 2/1984 | Rasberger | 260/958 |
| 5,216,052 | 6/1993 | Nesvadba et al. | 524/108 |
| 5,239,076 | 8/1993 | Meier et al. | 546/187 |
| 5,252,643 | 10/1993 | Nesvadba et al. | 524/111 |
| 5,405,891 | 4/1995 | Pitteloud | 524/102 |
| 5,439,958 | 8/1995 | Scrima et al. | 524/102 |
| 5,442,067 | 8/1995 | Pitteloud | 546/25 |
| 5,449,776 | 9/1995 | Vignali et al. | 544/198 |
| 5,457,199 | 10/1995 | Scrima et al. | 544/198 |
| 5,489,683 | 2/1996 | Borzatta et al. | 544/209 |
| 5,496,875 | 3/1996 | Borzatta et al. | 524/99 |

FOREIGN PATENT DOCUMENTS

| | | |
|---|---|---|
| 0042359 | 12/1981 | European Pat. Off. |
| 356688 | 3/1990 | European Pat. Off. |
| 0589842 | 3/1994 | European Pat. Off. |
| 591102 | 4/1994 | European Pat. Off. |
| 589839 | 9/1994 | European Pat. Off. |
| 2380290 | 9/1978 | France . |
| 3928291 | 2/1991 | Germany . |
| 4306747 | 9/1993 | Germany . |
| 4316876 | 11/1993 | Germany . |
| 4316622 | 11/1993 | Germany . |
| 4316611 | 11/1993 | Germany . |
| 553827 | 9/1974 | Switzerland . |
| 2247241 | 2/1992 | United Kingdom . |
| 2265377 | 9/1993 | United Kingdom . |

OTHER PUBLICATIONS

Houfen–Weyl, "Methoden der Organischen Chemie, Band E1, Organische Phosphorverbindungen", pp. 276–285 (1982).
R. Gachter et al. (Ed) Plastics Additives Handbook 3rd. Ed. p. 47 (1990).
T. Konig et al. L. Prabt. Chem. 334(1992) 333–349.
Chem. Abst. 91–21833t (1979) of FR 2,380,290.
Derw. Abst. 91–066407 of DE 3,928,291 (1991).
Org. Synthesis Coll. vol. IV 784 (1963).
Derw. Abst. 93–371074 of DE 4,316,611 (1993).
Chem. Abst. 120: 245507v of DD 301,615 (1994).
Th. Weil et al. Helv. Chim. Acta 1952, 1412–1413.
F. Nief et al. Tetrahedron vol. 47(33) 6673 (1991).
Ullmanns Enzyklapadie der Technischen Chemie, BD 13 Seiten 85–94 (1977).
Derw. Abst.—93–371073 of Germany (1993) 4316622.
Derw. Abst.—93–353775 of Germany 4,316,876 (1993).
Derw. Abst. 94–103409 of EP 589,839 (1994).

*Primary Examiner*—Amelia Owens
*Attorney, Agent, or Firm*—Michele Kovaleski

[57] ABSTRACT

The invention relates to novel compounds of the formula I

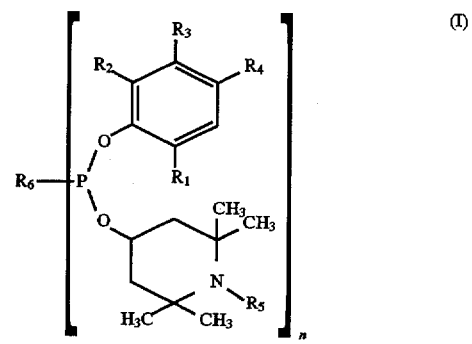

in which the general symbols are as defined in claim 1, as stabilizers for organic materials against oxidative, thermal or light-induced degradation.

16 Claims, No Drawings

HALS PHOSPHONITES AS STABILIZERS

The present invention relates to novel HALS phosphonites, to compositions comprising an organic material, preferably a polymer, and the novel HALS phosphonites, and to the use thereof for the stabilization of organic materials against oxidative, thermal or light-induced degradation.

Organic phosphites and phosphonites are known in industry as costabilizers, secondary antioxidants and processing stabilizers, inter alia for polyolefins; examples of such known phosphite and phosphonite stabilizers are given in R. Gächter/H. Müller (Eds.), Plastics Additives Handbook, 3rd Ed., p. 47, Hanser, Munich, 1990, and EP-A-356 688.

Hindered amines, including, in particular, compounds containing 2,2,6,6-tetramethylpiperidyl groups, are preferably used as light stabilizers (hindered amine light stabilizers, HALS).

Phosphites or phosphonites containing HALS structural units are described, for example, by T. König et al, J. prakt. Chem. 334, 333–349 (1992), in U.S. Pat. No. 5,239,076, GB-A-2 247 241, DE-A-4 306 747 and FR-A-2 380 290.

There continues to be a demand for effective stabilizers for organic materials which are sensitive to oxidative, thermal and/or light-induced degradation.

It has now been found that a selected group of such HALS phosphonites is particularly suitable as stabilizers for organic materials which are sensitive to oxidative, thermal or light-induced degradation. Particular emphasis should be made of the suitability of said compounds as processing stabilizers for synthetic polymers.

The present invention therefore relates to compounds of the formula I

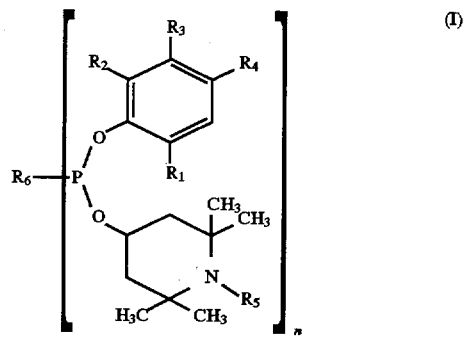

in which
$R_1$ and $R_2$, independently of one another, are hydrogen, $C_1$–$C_{25}$alkyl, $C_2$–$C_{24}$alkenyl, unsubstituted or $C_1$–$C_4$alkyl-substituted $C_5$–$C_8$cycloalkyl; unsubstituted or $C_1$–$C_4$alkyl-substituted phenyl; unsubstituted or $C_1$–$C_4$alkyl-substituted $C_5$–$C_8$cycloalkenyl; $C_7$–$C_9$phenylalkyl or —CH$_2$—S—R$_7$, $R_3$ is hydrogen or methyl, $R_4$ is hydrogen, $C_1$–$C_{25}$alkyl, $C_2$–$C_{24}$alkenyl, unsubstituted or $C_1$–$C_4$alkyl-substituted $C_5$–$C_8$cycloalkyl; unsubstituted or $C_1$–$C_4$alkyl-substituted phenyl; unsubstituted or $C_1$–$C_4$-alkyl-substituted $C_5$–$C_8$cycloalkenyl; $C_7$–$C_9$phenylalkyl, —CH$_2$—S—R$_7$, —(CH$_2$)$_p$COOR$_8$ or —(CH$_2$)$_q$OR$_9$, $R_5$ is hydrogen, $C_1$–$C_8$alkyl, O·, OH, NO, —CH$_2$CN, $C_1$–$C_{18}$alkoxy, $C_5$–$C_{12}$cycloalkoxy, $C_3$–$C_6$alkenyl, $C_3$–$C_6$alkynyl, $C_1$–$C_8$acyl, or $C_7$–$C_9$phenylalkyl which is unsubstituted or substituted on the phenyl ring by $C_1$–$C_4$alkyl; or $R_5$ furthermore is a radical of the formula II

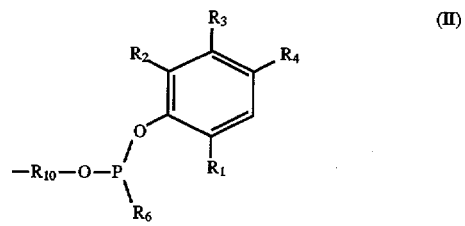

in which $R_6$ is as defined below for n=1, if n is 1, $R_6$ is $C_1$–$C_{25}$alkyl, $C_2$–$C_{24}$alkenyl, unsubstituted or $C_1$–$C_4$alkyl-substituted $C_5$–$C_8$cycloalkyl; unsubstituted or $C_1$–$C_4$-alkyl- or phenyl-substituted phenyl; unsubstituted or $C_1$–$C_4$alkyl-substituted $C_5$–$C_8$cycloalkenyl; or $C_7$–$C_9$phenylalkyl which is unsubstituted or substituted on the phenyl ring by $C_1$–$C_4$alkyl;

if n is 2, $R_6$ is a radical of the formula III,

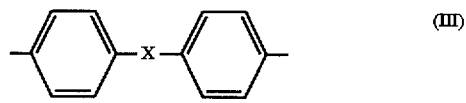

$R_7$ is $C_1$–$C_{18}$alkyl, unsubstituted or $C_1$–$C_4$alkyl-substituted $C_5$–$C_{12}$cycloalkyl; unsubstituted or $C_1$–$C_4$alkyl-substituted phenyl; $C_7$–$C_9$phenylalkyl or —(CH$_2$)$_r$COOR$_8$, $R_8$ is $C_1$–$C_{18}$alkyl, unsubstituted or $C_1$–$C_4$alkyl-substituted $C_5$–$C_{12}$cycloalkyl; unsubstituted or $C_1$–$C_4$alkyl-substituted phenyl; or $C_7$–$C_9$phenylalkyl;

$R_9$ is $C_1$–$C_{25}$alkyl, unsubstituted or $C_1$–$C_4$alkyl-substituted phenyl; $C_7$–$C_9$phenylalkyl, $C_1$–$C_{25}$alkanoyl, $C_3$–$C_{25}$alkenoyl, $C_2$–$C_{25}$alkanoyl which is interrupted by oxygen, sulfur or >N—R$_{11}$; $C_6$–$C_9$cycloalkylcarbonyl, unsubstituted or $C_1$–$C_{12}$alkyl-substituted benzoyl; thienoyl or furoyl, $R_{10}$ is $C_1$–$C_{18}$alkylene, $C_4$–$C_{18}$alkylene which is interrupted by oxygen, sulfur or >N—R$_{11}$; $C_4$–$C_{18}$alkenylene, phenylethylene,

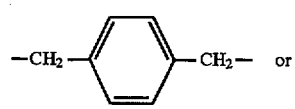

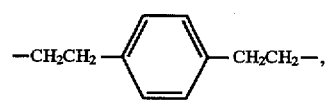

$R_{11}$ is hydrogen or $C_1$–$C_8$alkyl, $R_{12}$ and $R_{13}$, independently of one another, are hydrogen, CF$_3$, $C_1$–$C_{12}$alkyl or phenyl, or $R_{12}$ and $R_{13}$, together with the carbon atom to which they are bonded, form an unsubstituted or $C_1$–$C_4$alkyl-substituted $C_5$–$C_8$cycloalkylidene ring;

X is a direct bond, oxygen, sulfur or

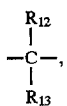

n is 1 or 2, p is 0, 1 or 2, q is an integer from 3 to 8, and r is 1 or 2.

Alkyl having up to 25 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl. One of the preferred meanings of $R_1$, $R_2$ and $R_4$ is, for example, $C_1$–$C_{18}$alkyl, in particular $C_1$–$C_{12}$alkyl, for example $C_1$–$C_8$alkyl. Particularly preferred meanings of $R_1$ and $R_2$ are methyl and tert-butyl. A particularly preferred meaning of $R_4$ is tert-butyl.

Alkenyl having 2 to 24 carbon atoms is a branched or unbranched radical, for example vinyl, propenyl, 2-butenyl, 3-butenyl, isobutenyl, n-2,4-pentadienyl, 3-methyl-2-butenyl, n-2-octenyl, n-2-dodecenyl, isododecenyl, oleyl, n-2-octadecenyl or n-4-octadecenyl. Preference is given to alkenyl having 3 to 18, in particular 3 to 12, carbon atoms.

Unsubstituted or $C_1$–$C_4$alkyl-substituted $C_5$–$C_{12}$cycloalkyl, in particular $C_5$–$C_8$cycloalkyl, which preferably contains 1 to 3, in particular 1 or 2, branched or unbranched alkyl radicals, is, for example, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl, cyclooctyl or cyclododecyl. Preference is given to $C_5$–$C_8$cycloalkyl, in particular cyclohexyl.

$C_1$–$C_4$alkyl-substituted phenyl, which preferably contains 1 to 3, in particular 1 or 2, alkyl groups, is, for example, o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

Unsubstituted or $C_1$–$C_4$alkyl-substituted $C_5$–$C_8$cycloalkenyl, which preferably contains 1 to 3, in particular 1 or 2, branched or unbranched alkyl radicals, is, for example, cyclopentenyl, methylcyclopentenyl, dimethylcyclopentenyl, cyclohexenyl, methylcyclohexenyl, dimethylcyclohexenyl, trimethylcyclohexenyl, tert-butylcyclohexenyl, cycloheptenyl or cyclooctenyl. Preference is given to cyclohexenyl.

$C_7$–$C_9$phenylalkyl which is unsubstituted or substituted on the phenyl radical by $C_1$–$C_4$alkyl and which preferably contains 1 to 3, in particular 1 or 2, branched or unbranched alkyl radicals is, for example, benzyl, α-methylbenzyl, α,α-dimethylbenzyl, 2-phenylethyl, 2-methylbenzyl, 3-methylbenzyl, 4-methylbenzyl, 2,4-dimethylbenzyl, 2,6-dimethylbenzyl or 4-tert-butylbenzyl. Benzyl is preferred.

Alkoxy having up to 18 carbon atoms is a branched or unbranched radical, for example methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy. Preference is given to alkoxy having 6 to 12 carbon atoms.

Cycloalkoxy having 5 to 12 carbon atoms is, for example, cyclopentoxy, cyclohexoxy, cycloheptoxy, cyclooctoxy, cyclodecyloxy or cyclododecyloxy. One of the preferred meanings of $R_5$ is $C_5$–$C_8$cycloalkoxy. Particular preference is given to cyclopentoxy and cyclohexoxy.

Alkynyl having 3 to 6 carbon atoms is a branched or unbranched radical; for example propynyl (propargyl, —$CH_2$—C≡CH ), 2-butynyl or 3-butynyl.

Acyl having 1 to 8 carbon atoms is, for example, formyl, acetyl, propionyl, butyryl, pentanoyl, hexanoyl, heptanoyl, octanoyl, benzoyl, acryloyl or crotonyl. Preference is given to $C_1$–$C_8$alkanoyl, $C_3$–$C_8$alkenoyl or benzoyl, in particular acetyl.

Alkanoyl having up to 25 carbon atoms is a branched or unbranched radical, for example formyl, acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, eicosanoyl or docosanoyl. Preference is given to alkanoyl having 2 to 18, in particular 2 to 12, for example 2 to 6, carbon atoms.

Alkenoyl having 3 to 25 carbon atoms is a branched or unbranched radical, for example propenoyl, 2-butenoyl, 3-butenoyl, isobutenoyl, n-2,4-pentadienoyl, 3-methyl-2-butenoyl, n-2-octenoyl, n-2-dodecenoyl, isododecenoyl, oleoyl, n-2-octadecenoyl or n-4-octadecenoyl. Preference is given to alkenoyl having 3 to 18, in particular 2 to 12, for example 2 to 6, carbon atoms.

$C_2$–$C_{25}$alkanoyl, in particular $C_3$–$C_{25}$alkanoyl, which is interrupted by oxygen, sulfur or >N—$R_{11}$ can be interrupted once or more than once and is, for example, $CH_3OCO$—$CH_3$—O—$CH_2CO$—, $CH_3$—S—$CH_2CO$—, $CH_3$—NH—$CH_2CO$—, $CH_3$—N($CH_3$)—$CH_2CO$—, $CH_3$—O—$CH_2CH_2$—O—$CH_2CO$—, $CH_3$—(O—$CH_2CH_2$—)$_2$—O—$CH_2CO$—, $CH_3$—(O—$CH_2CH_2$—)$_3$O—$CH_2CO$— or $CH_3$—(O—$CH_2CH_2$—)$_4$O—$CH_2CO$—.

$C_6$–$C_9$cycloalkylcarbonyl is, for example, cyclopentylcarbonyl, cyclohexylcarbonyl, cycloheptylcarbonyl or cyclooctylcarbonyl. Cyclohexylcarbonyl is preferred.

$C_1$–$C_2$alkyl-substituted benzoyl, which preferably contains 1 to 3, in particular 1 or 2, alkyl groups, is, for example, o-, m- or p-methylbenzoyl, 2,3-dimethylbenzoyl, 2,4-dimethylbenzoyl, 2,5-dimethylbenzoyl, 2,6-dimethylbenzoyl, 3,4-dimethylbenzoyl, 3,5-dimethylbenzoyl, 2-methyl-6-ethylbenzoyl, 4-tert-butylbenzoyl, 2-ethylbenzoyl, 2,4,6-trimethylbenzoyl, 2,6-dimethyl-4-tert-butylbenzoyl or 3,5-di-tert-butylbenzoyl.

$C_1$–$C_{18}$alkylene is a branched or unbranched radical, for example methylene, ethylene, propylene, tetramethylene, pentamethylene, hexamethylene, heptamethylene, octamethylene, decamethylene, dodecamethylene or octadecamethylene. Preference is given to $C_1$–$C_{12}$alkylene, in particular $C_1$–$C_8$alkylene. A preferred meaning of $R_{10}$ is ethylene and propylene.

$C_4$–$C_{18}$alkylene which is interrupted by oxygen, sulfur or >N—$R_{11}$ can be interrupted once or more than once and is, for example, —$CH_2CH_2$—O—$CH_2CH_2$—, —$CH_2CH_2$—S—$CH_2CH_2$—, —$CH_2CH_2$—NH—$CH_2CH_2$—, —$CH_2CH_2$—N($CH_3$)—$CH_2CH_2$—, —$CH_2CH_2$—O—$CH_2CH_2$—O—$CH_2CH_2$—, —$CH_2CH_2$—(O—$CH_2CH_2$—)$_2$—$CH_2CH_2$—, —$CH_2CH_2$—(O—$CH_2CH_2$—)$_3$O—$CH_2CH_2$—, —$CH_2CH_2$—(O—$CH_2CH_2$—)$_4$O—$CH_2CH_2$— or —$CH_2CH_2$—S—$CH_2CH_2$.

$C_4$–$C_8$alkenylene $R_{10}$ is, for example, 2-buten-1,4-ylene.

Phenylethylene is —$CH(C_6H_5)CH_2$—.

Unsubstituted or $C_1$–$C_4$alkyl-substituted $C_5$–$C_8$cycloalkylidene, which preferably contains 1 to 3, in particular 1 or 2, branched or unbranched alkyl radicals, is for example, cyclopentylidene, methylcyclopentylidene, dimethylcyclopentylidene, cyclohexylidene, methylcyclohexylidene, dimethylcyclohexylidene, trimethylcyclohexylidene, tert-butylcyclohexylidene, cycloheptylidene or cyclooctylidene. Preference is given to cyclohexylidene and tert-butylcyclohexylidene.

Preference is given to compounds of the formula I in which $R_1$ and $R_2$, independently of one another, are hydrogen, $C_1$–$C_{18}$alkyl, $C_2$–$C_{18}$alkenyl, $C_5$–$C_8$cycloalkyl, unsubstituted or $C_1$–$C_4$alkyl-substituted phenyl, $C_5$–$C_8$cycloalkenyl, $C_7$–$C_9$phenylalkyl or —$CH_2$—S—$R_7$, $R_4$ is hydrogen, $C_1$–$C_{18}$alkyl, $C_2$–$C_{18}$alkenyl, $C_5$–$C_8$cycloalkyl, unsubstituted or $C_1$–$C_4$alkyl-substituted phenyl; $C_5$–$C_8$-cycloalkenyl, $C_7$–$C_9$-phenylalkyl, —$CH_2$—S—$R_7$, —$(CH_2)_p COOR_8$ or —$(CH_2)_q OR_9$, $R_5$ is hydrogen, $C_1$–$C_4$alkyl, OH, —$CH_2CN$, $C_4$–$C_{18}$alkoxy, $C_5$–$C_{12}$cycloalkoxy, allyl, propargyl, acetyl or $C_7$–$C_9$phenylalkyl; or $R_5$ furthermore is a radical of the formula II

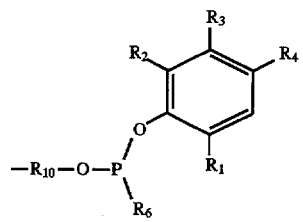

in which $R_6$ is as defined below for n=1, if n is 1, $R_6$ is $C_1$–$C_{18}$alkyl, $C_2$–$C_{18}$alkenyl, $C_5$–$C_8$cycloalkyl, unsubstituted or $C_1$–$C_4$alkyl— or phenyl-substituted phenyl; $C_5$–$C_8$cycloalkenyl or $C_7$–$C_9$phenylalkyl which is unsubstituted or substituted on the phenyl ring by 1 to 3 $C_1$–$C_4$alkyl;

$R_7$ is $C_1$–$C_{18}$alkyl, $C_5$–$C_{12}$cycloalkyl, unsubstituted or $C_1$–$C_4$alkyl-substituted phenyl; $C_7$–$C_9$phenylalkyl or —$(CH_2)_r COOR_8$, $R_8$ is $C_1$–$C_{18}$alkyl $C_5$–$C_{12}$cycloalkyl, unsubstituted or $C_1$–$C_4$alkyl-substituted phenyl; or $C_7$–$C_9$phenylalkyl, $R_9$ is $C_1$–$C_{18}$alkyl, unsubstituted or $C_1$–$C_4$alkyl-substituted phenyl; $C_7$–$C_9$phenylalkyl, $C_1$–$C_{18}$alkanoyl, $C_3$–$C_{18}$alkenoyl, $C_2$–$C_{18}$alkanoyl which is interrupted by oxygen, sulfur or >N—$R_{11}$; $C_6$–$C_9$cycloalkylcarbonyl, or unsubstituted or $C_1$–$C_4$alkyl-substituted benzoyl, $R_{10}$ is $C_1$–$C_{12}$alkylene, $C_4$–$C_{12}$alkylene which is interrupted by oxygen, sulfur or >N—$R_{11}$; $C_4$–$C_8$alkenylene,

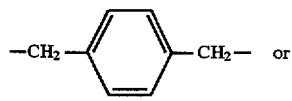

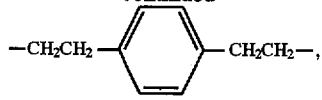

$R_{12}$ and $R_{13}$, independently of one another, are hydrogen, $CF_3$, $C_1$–$C_8$alkyl or phenyl, or $R_{12}$ and $R_{13}$, together with the carbon atom to which they are bonded, form a $C_5$–$C_8$cycloalkylidene ring.

Preference is also given to the compounds of the formula I in which $R_1$, $R_2$ and $R_4$, independently of one another, are hydrogen, $C_1$–$C_8$alkyl, cyclohexyl or phenyl.

Preference is likewise given to the compounds of the formula I in which $R_5$ is hydrogen, $C_1$–$C_4$alkyl, $C_4$–$C_{16}$alkoxy, $C_5$–$C_8$cycloalkoxy, allyl, propargyl, acetyl, benzyl or a radical of the formula II

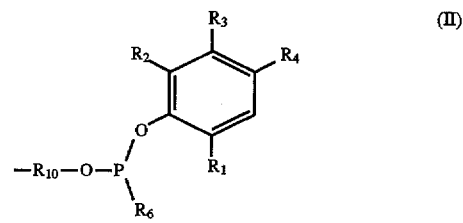

in which $R_6$ is unsubstituted or $C_1$–$C_4$alkyl-substituted phenyl, and $R_{10}$ is $C_1$–$C_4$alkylene.

Particular preference is given to the compounds of the formula I in which $R_1$ and $R_2$, independently of one another, are hydrogen, $C_1$–$C_{12}$alkyl, $C_2$–$C_{12}$alkenyl, cyclohexyl, phenyl, cyclohexenyl or benzyl, $R_4$ is hydrogen, $C_1$–$C_{12}$alkyl, $C_2$–$C_{12}$alkenyl, cyclohexyl, phenyl, cyclohexenyl, benzyl, —$CH_2$—S—$R_7$, —$(CH_2)_p COOR_8$ or —$(CH_2)_q OR_9$, $R_5$ is hydrogen, $C_1$–$C_4$alkyl, $C_4$–$C_{16}$alkoxy, $C_5$–$C_8$cycloalkoxy, allyl, propargyl, acetyl or benzyl; or $R_5$ furthermore is a radical of the formula II

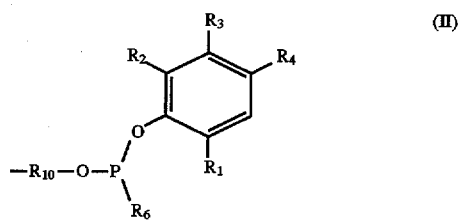

in which $R_6$ is as defined below for n=1, if n is 1, $R_6$ is $C_1$–$C_{12}$alkyl, $C_2$–$C_{12}$alkenyl, cyclohexyl, unsubstituted or $C_1$–$C_4$alkyl-substituted phenyl; cyclohexenyl or benzyl;

$R_7$ is $C_1$–$C_{12}$alkyl, $C_5$–$C_8$cycloalkyl, phenyl, benzyl or —$(CH_2)_r COOR_8$, $R_8$ is $C_1$–$C_{12}$alkyl, $C_5$–$C_8$cycloalkyl, phenyl or benzyl, $R_9$ is $C_1$–$C_{12}$alkyl, phenyl, benzyl, $C_1$–$C_2$alkanoyl, $C_2$–$C_{12}$alkanoyl which is interrupted by oxygen; cyclohexylcarbonyl or benzoyl, $R_{10}$ is $C_1$–$C_8$alkylene, $C_4$–$C_8$alkylene which is interrupted by oxygen, or $C_4$–$C_8$alkenylene, $R_{12}$ and $R_{13}$, independently of one another, are hydrogen, $CF_3$ or $C_1$–$C_4$alkyl, or $R_{12}$ and $R_{13}$, together with the carbon atom to which they are bonded, form a cyclohexylidene ring;

X is a direct bond, oxygen or $$-\underset{\underset{R_{13}}{|}}{\overset{\overset{R_{12}}{|}}{C}}-,$$

p is 2, q is an integer from 3 to 6, and r is 1.

Of particular interest are the compounds of the formula I in which $R_1$ and $R_2$, independently of one another, are hydrogen, $C_1$–$C_8$alkyl, cyclohexyl or phenyl, $R_4$ is hydrogen, $C_1$–$C_8$alkyl, cyclohexyl or —$(CH_2)_p COOR_8$, $R_5$ is hydrogen, $C_1$–$C_4$alkyl, $C_6$–$C_{12}$alkoxy, acetyl or benzyl; or $R_5$ furthermore is a radical of the formula II $$\text{(II)}$$

in which $R_6$ is as defined below for n=1, if n is 1, $R_6$ is $C_1$–$C_{12}$alkyl, cyclohexyl, phenyl or benzyl;

$R_8$ is $C_1$–$C_{12}$alkyl or benzyl, $R_{10}$ is $C_1$–$C_8$alkylene or $C_4$–$C_8$alkylene which is interrupted by oxygen, $R_{12}$ and $R_{13}$, independently of one another, are hydrogen or $C_1$–$C_4$alkyl, or $R_{12}$ and $R_{13}$, together with the carbon atom to which they are bonded, form a cyclohexylidene ring;

X is a direct bond or $$-\underset{\underset{R_{13}}{|}}{\overset{\overset{R_{12}}{|}}{C}}-,$$

and p is 2.

Of specific interest are the compounds of the formula I in which $R_1$ and $R_2$, independently of one another, are $C_1$–$C_4$alkyl, $R_3$ is hydrogen, $R_4$ is $C_1$–$C_4$alkyl, $R_5$ is methyl or a radical of the formula II $$\text{(II)}$$

in which $R_6$ is as defined below for n=1, if n is 1, $R_6$ is phenyl, if n is 2, $R_6$ is a radical of the formula III $$\text{(III)}$$

$R_{10}$ is ethylene,

X is a direct bond, and n is 1 or 2.

The novel compounds of the formula I can be prepared in a manner known per se.

For example, and this is preferred, a dichlorophosphine of the formula IV is reacted with a phenol of the formula V $$\text{(IV)}$$

$$\text{(V)}$$

$$\text{(VI)}$$

in which n, $R_6$, $R_1$, $R_2$, $R_3$ and $R_4$ are as defined above, to give an intermediate of the formula VII, or a dichlorophosphine of the formula IV is reacted with a piperidinol of the formula VI in which $R_5$ is as defined above, to give an intermediate of the formula VIII $$\text{(VII)}$$

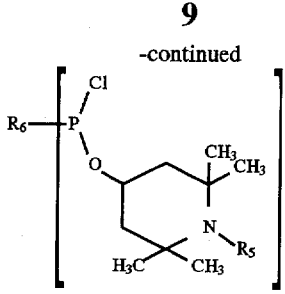

(VIII)

The intermediate of the formula VII is subsequently reacted with a piperidinol of the formula VI, and the intermediate of the formula VIII is reacted with a phenol of the formula V to give the novel compounds.

Preferably, the dichlorophosphine of the formula IV is first reacted with a phenol of the formula V.

The intermediates of the formulae VII and VIII are expediently not isolated and are reacted, without purification, with a piperidinol of the formula VI or a phenol of the formula V with elimination of hydrochloric acid to give the novel compounds of the formula I.

If n is 1 in the compound of the formula IV, both the phenol of the formula V and the piperidinol of the formula VI are preferably employed in equimolar mounts with respect to the dichlorophosphine of the formula IV.

If n is 2 in the compound of the formula IV, two equivalents, with respect to the dichlorophosphine of the formula IV employed, of each of the phenol of the formula V and of the piperidinol of the formula VI are preferably used.

In the reaction of the intermediates of the formulae VII and VIII to give the novel compounds of the formula I, the piperidinol of the formula VI or the phenol of the formula V is expediently used in a slight excess.

The reaction of the dichlorophosphine of the formula IV in the presence of a mixture comprising a phenol of the formula V and a piperidinol of the formula VI likewise gives the novel compounds of the formula I.

The reaction is carried out in the melt or in the presence of a suitable organic, polar or apolar, aprotic solvent. This reaction is preferably carried out in the presence of a base at temperatures between −20° C. and the boiling point of the solvent, in particular at temperature between 20° and 150° C.

Bases such as amines can simultaneously also be used as solvent.

The base can be employed in various amounts, from catalytic via stoichiometric amounts up to an excess of several times the molar amount with respect to the compounds of the formula IV, V or VI employed. The hydrogen chloride formed during the reaction is, if appropriate, converted through the base into chloride, which can be removed by filtration and/or washing with a suitable aqueous or solid phase; a second, water-immiscible solvent can also be employed here. The products are expediently isolated by evaporating the organic phase and drying the residue.

Suitable solvents for carrying out the reaction include hydrocarbons (for example mesitylene, toluene, xylene, hexane, pentane or other petroleum ether fractions), halogenated hydrocarbons (for example di- or trichloromethane, 1,2-dichloroethane, 1,1,1-trichloroethane or chlorobenzene), ethers (for example diethyl ether, dibutyl ether or tetrahydrofuran), ketones (for example acetone, ethyl methyl ketone, diethyl ketone, methyl propyl ketone or cyclohexanone), furthermore acetonitrile, butyl acetate, dimethyl formamide, dimethyl sulfoxide or N-methylpyrrolidone.

Suitable bases include primary, secondary and in particular tertiary amines (for example trimethylamine, triethylamine, tributylamine, N,N-dimethylaniline, N,N-diethylaniline or pyridine), hydrides (for example lithium hydride, sodium hydride or potassium hydride) or alkoxides (for example sodium methoxide).

If hydrides (for example sodium hydride, sodium borohydride or lithium aluminium hydride), alkali metals, alkali metal hydroxides or sodium methoxide are used as bases, the corresponding alkoxide of the compound of the formula V or VI can first be formed; any reaction product formed (for example water or methanol) is removed by distillation (for example as an azeotrope with toluene) before the reaction with the compound of the formula IV.

The compounds of the formula IV are known or can be prepared by processes known per se, as described, for example, in Org. Syntheses Coll. Vol. IV, 784 (1963) or by Th. Weil et at, Helv. Chim. Acta 1952, 1412 or F. Nief et al, Tetrahedron 47 (33), 6673 (1991).

The compounds of the formula IV required for the preparation of the novel compounds of the formula I can be prepared in situ analogously to the abovementioned literature procedures, and reacted further, without isolation, with the compounds of the formulae V and VI to give the compounds of the formula I.

The phenols of the formula V are known or can be prepared by processes known per se.

The HALS compounds of the formula VI are known or can be prepared by processes known per se, as described, for example, in U.S. Pat. No. 4,233,412.

Compounds of the formula I in which $R_5$ is a radical of the formula II are prepared, for example, by reacting two equivalents of the intermediate of the formula VII with one equivalent of the HALS-diol compound of the formula IX

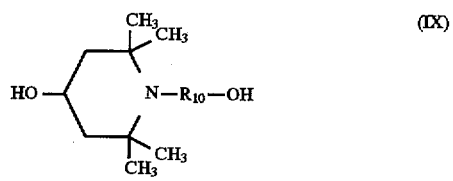

(IX)

in which $R_{10}$ is as defined above.

The preferred reaction conditions, for example temperature, solvent, base or catalyst, correspond to those as described above.

The HALS-diol compounds of the formula IX are known or can be prepared by processes known per se, as described, for example, in U.S. Pat. No. 4,233,412.

The novel compounds of the formula I are suitable for the stabilization of organic materials against oxidative, thermal or light-induced degradation.

EXAMPLES OF SUCH MATERIALS ARE

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:
a) radical polymerisation (normally under high pressure and at elevated temperature).
b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titaninm(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

5. Polystyrene, poly(p-methylstyrene), poly(a-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The invention therefore furthermore relates to compositions comprising (a) an organic material subjected to oxidative, thermal or light-induced degradation and (b) at least one compound of the formula I.

The organic materials to be protected are preferably natural, semisynthetic or preferably synthetic organic materials. Particular preference is given to thermoplastic polymers, in particular PVC or polyolefins, in particular polyethylene and polypropylene.

Particular emphasis should be placed on the action of the novel compounds against thermal and oxidative degradation, in particular on heating, as occurs in the processing of thermoplastics. The novel compounds are therefore highly suitable for use as processing stabilizers.

The compounds of the formula I are preferably added to the material to be stabilized in amounts of from 0.01 to 10%, for example from 0.01 to 5%, preferably from 0.025 to 3%, in particular from 0.025 to 1%, based on the weight of the organic material to be stabilized.

In addition to the compounds of the formula I, the novel compositions can contain further costabilizers, for example the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-di-methyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-do-decylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl) disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl- 2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl)

dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3, 5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.7. O-, N- and S-benzyl compounds, for example 3,5,3', 5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis (octylmercapto)-6-(3,5-di-tert-butyl-4-hydroxyanilino)-1,3, 5-triazine, 2-octylmercapto-4,6-bis(3,5-di-tert-butyl-4-hydroxyanilino)-1,3,5-triazine, 2-octylmercapto-4,6-bis(3, 5-di-tert-butyl-4-hydroxyphenoxy)-1,3,5-triazine, 2,4,6-tris (3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl13,5-di-tert-butyl- 4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of δ-(3,5-dicyclohexyl4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl) trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$-]$_2$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis (4-tert-butylbenzoyl)resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5- di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-δ-methyl-p-methoxy-cinnamate, methyl α-carbomethoxy-p-methoxycinnamate and N-(β-carbomethoxyβ-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy-2,2,6,6-tetramethylpiperidyl) sebacate, bis(1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl) pyrrolidine-2,5-dione.

2.7. Oxamides, for example 4,4'-dioctyloxyoxanilide, 2,2'-diethoxyoxanilide, 2,2'-dioctyloxy- 5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoly dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methylphosphite, bis(2,4-di-tert-butyl-6-methylphenyl) ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticisers, lubricants, emulsifiers, pigments, optical brighteners, flameproofing agents, antistatic agents and blowing agents.

11. Benzofuranones and indolinones, for example those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4 316 611, DE-A-4 316 622, DE-A-4 316 876, EP-A-0 589 839 or EP-A-0 591 102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7- di-tert-butyl-3-(4-[2-hydroxyethoxy]-phenylbenzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloloxyphenyl)-5,7-di-tert-butyl-benzofuran-2-one.

The costabilizers, with the exception of the benzofuranones mentioned under point 11, are added, for example, in concentrations of from 0.01 to 10%, based on the total weight of the material to be stabilized.

Other preferred compositions comprise, in addition to component (a) add the compounds of the formula I, other additives, in particular phenolic antioxidants, light stabilizers and/or processing stabilizers.

Particularly preferred additives are phenolic antioxidants (point 1 in the list), sterically hindered mines (point 2.6 in the list), phosphites and phosphonites (point 4 in the list) and peroxide scavengers (point 5 in the list).

Other additives (stabilizers) which are likewise particularly preferred are benzofuran-2-ones, as described, for example, in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4 316 611, DE-A-4 316 622, DE-A-4 316 876, EP-A-0 589 839 and EP-A-0 591 102.

Examples of such benzofuran-2-ones are compounds of the formula

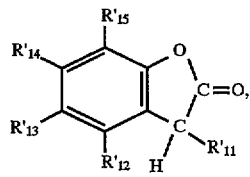

in which

R'$_{11}$ is an unsubstituted or substituted carbocyclic or heterocyclic aromatic ring system, R'$_{12}$ is hydrogen;

R'$_{14}$ is hydrogen, alkyl having 1 to 12 carbon atoms, cyclopentyl, cyclohexyl or chlorine;

R'$_{13}$ is as defined for R'$_{12}$ or R'$_{14}$ or is a radical of the formula

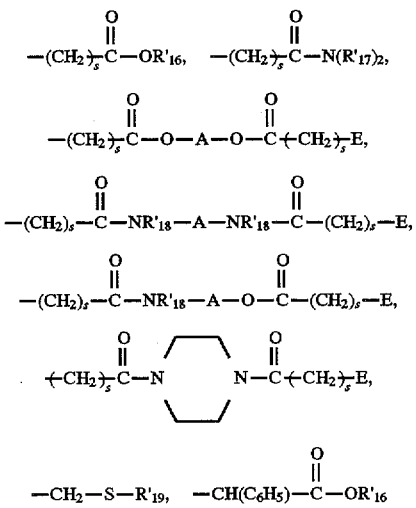

or —D—E, in which

R'$_{16}$ is hydrogen, alkyl having 1 to 18 carbon atoms, alkyl having 2 to 18 carbon atoms which is interrupted by oxygen or sulfur, dialkylaminoalkyl having a total of 3 to 16 carbon atoms, cyclopentyl, cyclohexyl, phenyl or phenyl which is substituted by 1 to 3 alkyl radicals having a total of at most 18 carbon atoms;

s is 0, 1 or 2;

the substituents R'$_{17}$, independently of one another, are hydrogen, alkyl having 1 to 18 carbon atoms, cyclopentyl, cyclohexyl, phenyl, phenyl which is substituted by 1 or 2 alkyl radicals having a total of at most 16 carbon atoms, a radical of the formula —C$_2$H$_4$OH, —C$_2$H$_4$—O—C$_t$H$_{2t+1}$ or

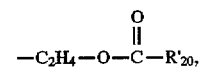

or, together with the nitrogen atom to which they are bonded, form a piperidine or morpholine radical;

t is from 1 to 18;

R'$_{20}$ is hydrogen, alkyl having 1 to 22 carbon atoms or cycloalkyl having 5 to 12 carbon atoms;

A is alkylene having 2 to 22 carbon atoms which may be interrupted by nitrogen, oxygen or sulfur;

R'$_{18}$ is hydrogen, alkyl having 1 to 18 carbon atoms, cyclopentyl, cyclohexyl, phenyl, phenyl which is substituted by 1 or 2 alkyl radicals having a total of at most 16 carbon atoms, or benzyl;

R'$_{19}$ is alkyl having 1 to 18 carbon atoms;

D is —O—, —S—, —SO—, —SO$_2$— or —C(R'$_{21}$)$_2$—;

the substituents R'$_{21}$, independently of one another, are hydrogen, C$_1$–C$_{16}$alkyl, where the two R'$_{21}$ radicals together contain 1 to 16 carbon atoms, R'$_{21}$ is furthermore phenyl or a radical of the formula

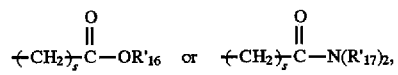

in which s, R'$_{16}$ and R'$_{17}$ are as defined above;

E is a radical of the formula

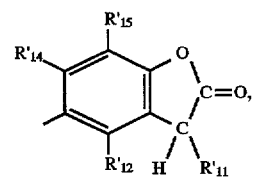

in which R'$_{11}$, R'$_{12}$ and R'$_{14}$ are as defined above; and

R'$_{15}$ is hydrogen, alkyl having 1 to 20 carbon atoms, cyclopentyl, cyclohexyl, chlorine or a radical of the formula

in which R'$_{16}$ and R'$_{17}$ are as defined above, or R'$_{15}$ together with R'$_{14}$ forms a tetramethylene radical.

Preference is given to benzofuran-2-ones in which R'$_{13}$ is hydrogen, alkyl having 1 to 12 carbon atoms, cyclopentyl, cyclohexyl, chlorine or a radical of the formula

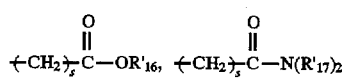

or —D—E, in which s, R'₁₆, R'₁₇, D and E are as defined above, and R'₁₆ is, in particular, hydrogen, alkyl having 1 to 18 carbon atoms, cyclopentyl or cyclohexyl.

Preference is also given to benzofuran-2-ones in which R'₁₁ is phenyl or phenyl which is substituted by 1 or 2 alkyl radicals having a total of at most 12 carbon atoms; R'₁₂ is hydrogen; R'₁₄ is hydrogen or alkyl having 1 to 12 carbon atoms; R'₁₃ is hydrogen, alkyl having 1 to 12 carbon atoms,

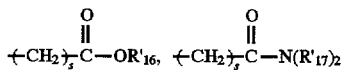

or —D—E;

R'₁₅ is hydrogen, alkyl having 1 to 20 carbon atoms,

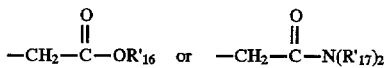

or R'₁₅ together with R'₁₄ forms a tetramethylene radical, where s, R'₁₆, R'₁₇, D and E are as defined at the outset.

Likewise of particular interest are benzofuran-2-ones in which R'₁₃ is hydrogen, alkyl having 1 to 12 carbon atoms or —D—E; R'₁₂ and R'₁₄, independently of one another, are hydrogen or alkyl having 1 to 4 carbon atoms; and R'₁₅ is alkyl having 1 to 20 carbon atoms, where D and E are as defined at the outset.

Finally, likewise of particular interest are benzofuran-2-ones in which R'₁₃ is alkyl having 1 to 4 carbon atoms or —D—E; R'₁₂ and R'₁₄ are hydrogen; and R'₁₅ is alkyl having 1 to 4 carbon atoms, cyclopentyl or cyclohexyl, where D is a —C(R'₂₁)₂— group and E is a radical of the formula

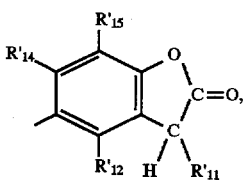

where the substituents R'₂₁ are identical or different and are each alkyl having 1 to 4 carbon atoms, and R'₁₁, R'₁₂, R'₁₄ and R'₁₅ are as defined above.

The amount of benzofuran-2-ones additionally employed can vary within broad limits. For example, they can be present in the novel compositions in amounts of from 0.0001 to 5% by weight, preferably from 0.001 to 2% by weight, in particular from 0.01 to 2% by weight.

The compounds of the formula I and any further additives are incorporated into the polymeric, organic material by known methods, for example before or during shaping or alternatively by application of the dissolved or dispersed compounds to the polymeric, organic material, if necessary with subsequent evaporation of the solvent. The novel compounds of the formula I can also be added to the materials to be stabilized in the form of a master-batch, which contains these in, for example, a concentration from 2.5 to 25% by weight.

The novel compounds of the formula I can also be added before or during polymerization or before crosslinking.

The compounds of the formula I can be incorporated into the material to be stabilized in pure form or in encapsulated in waxes, oils or polymers.

The compounds of the formula I can also be sprayed onto the polymer to be stabilized. They are capable of diluting other additives (for example the conventional additives mentioned above) or their melts, so that they can also be sprayed onto the polymer to be stabilized together with these additives. A particularly advantageous method is the addition by spraying during deactivation of the polymerization catalysts, where, for example, the steam used for deactivation can be used for the spraying.

In the case of polyolefins polymerized in bead form, it may, for example, be advantageous to apply the novel compounds of the formula I, if desired together with other additives, by spraying.

The materials stabilized in this way can be used in a very wide variety of forms, for example as films, fibres, tapes, moulding compositions, profiles or as binders for paints, adhesives or adhesive cements.

As mentioned above, the organic materials to be protected are preferably organic polymers, particularly synthetic polymers. Thermoplastic materials, in particular polyolefins, are particularly advantageously protected. In particular, the excellent activity of the compounds of the formula I as processing stabilizers (heat stabilizers) should be emphasized. For this purpose, they are advantageously added to the polymer before or during processing thereof. However, other polymers (for example elastomers) or lubricants or hydraulic fluids can also be stabilized against degradation, for example light-induced or thermo-oxidative degradation. Elastomers are given in the above list of possible organic materials.

Suitable lubricants and hydraulic fluids are based, for example, on mineral or synthetic oils or mixtures thereof. The lubricants are known to the person skilled in the art and are described in the relevant specialist literature, for example in Dieter Klamann "Schmierstoffe und verwandte Produkte" [Lubricants and Related Products] (Verlag Chemie, Weingheim, 1982), in Schewe-Kobek, "Das Schmiermittel-Taschenbuch" [The Lubricant Handbook] (Dr. Alfred H üthig-Verlag, Heidelberg, 1974) and in "Ullmanns Enzyklop ädie der technischen Chemie" [Ullmann's Encyclopedia of Industrial Chemistry], Vol. 13, pages 85–94 (Verlag Chemie, Weinheim, 1977).

A preferred embodiment of the present invention is therefore the use of compounds of the formula I for the stabilization of organic materials against oxidative, thermal or light-induced degradation.

The novel compounds of the formula I are distinguished by pronounced excellent hydrolysis stability and advantageous colouring behaviour, ie low discoloration of the organic materials during processing.

Organic materials which have been stabilized by means of the compounds of the present invention are particularly well protected against light-induced degradation.

The present invention therefore also relates to a process for the stabilization of an organic material against oxidative, thermal or light-induced degradation, which comprises incorporating or applying at least one compound of the formula I into or to this material.

The examples below illustrate the invention in greater detail. Parts and percentages are by weight.

EXAMPLE 1

Preparation of the compound (101) (Table 1).

A solution of 7.71 g (35.0 mmol) of 2,4-di-tert-butyl-6-methylphenol in 120 ml of toluene is added dropwise at 10°

C. to a stirred solution, under a nitrogen atmosphere, of 6.26 g (35.0 mmol) of phenyldichlorophosphine and 4.25 g (42.0 mmol) of triethylamine in 50 ml of toluene. The cloudy mixture obtained is stirred at room temperature for 1 hour. The reaction mixture is cooled to 10° C., 4.25 g (42.0 mmol) of triethylamine are added, and a solution of 6.59 g (38.5 mmol) of 1,2,2,6,6-pentamethylpiperidin-4-ol in 30 ml of toluene is added dropwise. The white suspension is stirred at room temperature for 2.5 hours and filtered through Celite, and the filtrate is evaporated on a vacuum rotary evaporator. Chromatography of the residue on silica gel using the eluent system hexane/ethyl acetate 19:1 to 9:1 gives 10.0 g (57%) of compound (101) as a colourless oil (Table 1).

EXAMPLE 2

Preparation of compound (102) (Table 1).

5.4 ml (40.0 mmol) of phenyldichlorophosphine are added dropwise to a stirred solution, under a nitrogen atmosphere, of 8.81 g (40.0 mmol) of 2,6-di-tert-butyl-4-methylphenol in 28 ml (0.20 mol) of triethylamine. The yellow suspension is stirred at 95° C. for 24 hours. The reaction mixture is subsequently diluted with 50 ml of toluene, and a solution of 7.5 g (44.0 mmol) of 1,2,2,6,6-pentamethylpiperidin-4-ol in 50 ml of toluene is added dropwise. The reaction mixture is stirred at 80° C. for 10 hours. The suspension, cooled to room temperature, is filtered through Celite, and the filtrate is evaporated on a vacuum rotary evaporator. Chromatography of the residue on silica gel using the eluent system hexane/ethyl acetate 19:1 to 3:1 gives 5.5 g (37%) of compound (102). Crystallization from isopropanol gives a white powder, m.p. 85°–87° C. (Table 1).

EXAMPLE 3

Preparation of compound (103) (Table 1).

5.4 ml (40.0 mmol) of phenyldichlorophosphine are added dropwise at 10° C. to a stirred solution, under a nitrogen atmosphere, of 8.81 g (40.0 mmol) of 2,4-di-tert-butyl-6-methylphenol and 4.86 g (48.0 mmol) of triethylamine in 100 ml of toluene. The suspension is stirred at 95° C. for 4 hours. The reaction mixture is subsequently cooled to 10° C., 4.86 g (48.0 mmol) of triethylamine are added, and a solution of 4.03 g (20.0 mmol) of N-2'hydroxyethyl-4-hydroxy-2,2,6,6-tetramethyl-piperidine in 40 ml of tetrahydrofuran is added dropwise. The white suspension is stirred at room temperature for 1 hour and filtered through Celite, and the filtrate is evaporated on a vacuum rotary evaporator. The residue is taken up in 50 ml of toluene and re-filtered. Evaporation of the toluene on a vacuum rotary evaporator and drying of the residue in a high vacuum gives 14.7 g (86%) of compound (103), m.p. 47° C. (Table 1).

EXAMPLE 4

Preparation of compound (104) (Table 1).

A solution of 12.34 g (56.0 mmol) of 2,4-di-tert-butyl-6-methylphenol in 80 ml of toluene is added dropwise at 10° C. to a stirred solution, under a nitrogen atmosphere, of 9.96 g (28.0 mmol) of 4,4'-diphenyl(Bisdichlorophosphine) [see CH-A-553 827, column 3, lines 47–59] and 9.36 g (67.2 mmol) of triethylamine in 30 ml of toluene. The slightly yellow suspension is stirred at 60° C. for 1 hour and cooled to 10° C. 9.36 g (67.2 mmol) of triethylamine are added, and a solution of 9.59 g (56.0 mmol) of 1,2,2,6,6-pentamethylpiperidin-4-ol in 80 ml of toluene is subsequently added dropwise. The reaction mixture is stirred at room temperature for 1 hour and at 60° C. for 1 hour. The suspension, cooled to room temperature, is filtered through Celite, and the filtrate is evaporated on a vacuum rotary evaporator. Chromatography of the residue on silica gel using the eluent system hexane/ethyl acetate 19:1 to :1:1 gives 10.0 g (36%) of compound (104), m.p. 83°–86° C., as an amorphous powder (Table 1).

TABLE 1

| No. | Compound | m.p. (°C.) | C(%), H(%), N (%) (calculated/found) | $^{31}$P-NMR (CDCl$_3$) (ppm) |
|---|---|---|---|---|
| 101 | 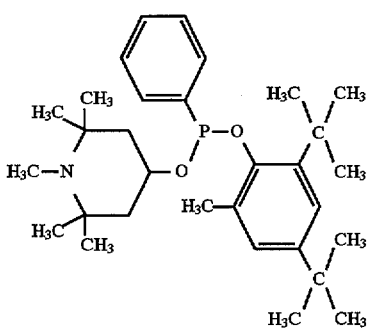 | Oil | 74.81  9.72  2.81<br>75.75  10.03  2.66 | 162.32 |

TABLE 1-continued

| No. | Compound | m.p. (°C.) | C(%), H(%), N (%) (calculated/found) | | | $^{31}$P-NMR (CDCl$_3$) (ppm) |
|---|---|---|---|---|---|---|
| 102 | [structure] | 85–87 | 74.81 74.94 | 9.72 9.92 | 2.81 2.47 | 170.21 |
| 103 | [structure] | 47 | 74.53 74.52 | 9.09 9.16 | 1.64 1.40 | 162.5 158.8 |
| 104 | [structure] | 83–86 | 74.96 74.40 | 9.54 9.63 | 2.82 2.57 | 162.55 |

EXAMPLE 5

Stabilization of polypropylene during multiple extrusion.

1.3 kg of polypropylene powder (®Profax 6501) which has been prestabilized by means of 0.025% of Irganox® 1076 (n-octadecyl (3-[3,5-di-tert-butyl-4-hydroxyphenyl] propionate) (having a melt flow index of 3.2, measured at 230° C. and 2.16 kg) are mixed with 0.05% of Irganox® 1010 (pentaerythrityl tetrakis [3-(3,5-di-tert-butyl-4-hydroxyphenyl)propionate]), 0.05% of calcium stearate, 0.03% of dihydrotalcite [DHT 4A®, Kyowa Chemical Industry Co., Ltd., Mg$_{4.5}$Al$_2$(OH)$_{13}$ CO$_3$.3.5 H$_2$O] and 0.05% of the compound from Table 1. This mixture is extruded in an extruder having a barrel diameter of 20 mm and a length of 400 mm at 100 revolutions per minute, the three heating zones being set at the following temperatures: 260°, 270°, 280° C. The extrudate is cooled by drawing through a water bath and subsequently granulated. These granules are re-extruded. After 3 extrusions, the melt flow index is measured (at 230° C. and 2.16 kg). A large increase in the melt flow index means considerable chain degradation, ie poor stabilization. The results are shown in Table 2.

TABLE 2

| Compound from Table 1 | Melt flow index after 3 extrusions |
|---|---|
| — | 20.0 |
| 101 | 4.6 |
| 102 | 4.8 |
| 103 | 4.7 |
| 104 | 5.4 |

EXAMPLE 6

Stabilization of polyethylene during processing.

100 parts of polyethylene powder (Lupolen® 5260 Z) are mixed with 0.05 part of Irganox® 1010 (pentaerythrityl tetrakis[3-(3,5-di-tert-butyl-4-hydroxyphenyl)propionate]) and 0.1 part of stabilizer from Table 1, and the mixture is compounded in a Brabender Plastograph at 220° C. and 50 revolutions per minute. During this time, the compounding resistance is recorded continuously as torque. During the compound time, the polymer, after an extended constant time, begins to cross link, which is evident from the rapid increase in torque. Table 3 shows the time before significant increase in the torque as a measure of the stabilizer action. The longer this time, the better the stabilizer action.

TABLE 3

| Compound from Table 1 | Time before torque increase (min.) |
|---|---|
| — | 5.0 |
| 101 | 17.0 |
| 102 | 16.5 |

What is claimed is:

1. A compound of the formula I

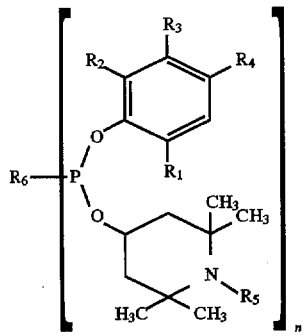

(I)

in which $R_1$ and $R_2$, independently of one another, are hydrogen, $C_1$–$C_{25}$alkyl, $C_2$–$C_{24}$alkenyl, unsubstituted or $C_1$–$C_4$alkyl-substituted $C_5$–$C_8$cycloalkyl; unsubstituted or $C_1$–$C_4$alkyl-substituted phenyl; unsubstituted or $C_1$–$C_4$alkyl-substituted $C_5$–$C_8$cycloalkenyl; $C_7$–$C_9$phenylalkyl or —CH$_2$—S—R$_7$, $R_3$ is hydrogen or methyl, $R_4$ is hydrogen, $C_1$–$C_{25}$alkyl, $C_2$–$C_{24}$alkenyl, unsubstituted or $C_1$–$C_4$alkyl-substituted $C_5$–$C_8$cycloalkyl; unsubstituted or $C_1$–$C_4$alkyl-substituted phenyl; unsubstituted or $C_1$–$C_4$alkyl-substituted $C_5$–$C_8$cycloalkenyl; $C_7$–$C_9$phenylalkyl, —CH$_2$—S—R$_7$, —(CH$_2$)$_p$COOR$_8$ or —(CH$_2$)$_q$OR$_9$, $R_5$ is hydrogen, $C_1$–$C_8$alkyl, O., OH, NO, —CH$_2$CN, $C_1$–$C_{18}$alkoxy, $C_5$–$C_{12}$cycloalkoxy, $C_3$–$C_6$alkenyl, $C_3$–$C_6$alkynyl, $C_1$–$C_8$acyl, or $C_7$–$C_9$phenylalkyl which is unsubstituted or substituted on the phenyl ring by $C_1$–$C_4$alkyl; or $R_5$ furthermore is a radical of the formula II

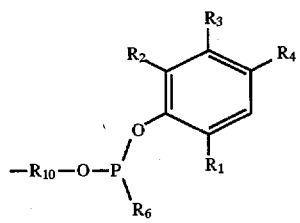

(II)

in which $R_6$ is as defined below for n=1, if n is 1, $R_6$ is $C_1$–$C_{25}$alkyl, $C_2$–$C_{24}$alkenyl, unsubstituted or $C_1$–$C_4$alkyl-substituted $C_5$–$C_8$cycloalkyl; unsubstituted or $C_1$–$C_4$alkyl- or phenyl-substituted phenyl; unsubstituted or $C_1$–$C_4$-alkyl-substituted $C_5$–$C_8$cycloalkenyl; or $C_7$–$C_9$phenylalkyl which is unsubsidized or substituted on the phenyl ring by $C_1$–$C_4$alkyl;

if n is 2, $R_6$ is a radical of the formula III

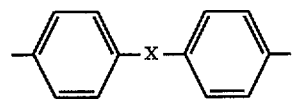

(III)

$R_7$ is $C_1$–$C_{18}$alkyl, unsubstituted or $C_1$–$C_4$alkyl-substituted $C_5$–$C_{12}$cycloalkyl; unsubstituted or $C_1$–$C_4$alkyl-substituted phenyl; $C_7$–$C_9$phenylalkyl or —(CH$_2$)$_r$COOR$_8$, $R_8$ is $C_1$–$C_{18}$alkyl, unsubstituted or $C_1$–$C_4$alkyl-substituted $C_5$–$C_{12}$cycloalkyl; unsubstituted or $C_1$–$C_4$alkyl-substituted phenyl; or $C_7$–$C_9$phenylalkyl, $R_9$ is $C_1$–$C_{25}$alkyl, unsubstituted or $C_1$–$C_4$alkyl-substituted phenyl; $C_7$–$C_9$phenylalkyl, $C_1$–$C_{25}$alkanoyl, $C_3$–$C_{25}$alkenoyl, $C_2$–$C_{25}$alkanoyl which is interrupted by oxygen, sulfur or >N—R$_{11}$; $C_6$–$C_9$cycloalkylcarbonyl, unsubstituted or $C_1$–$C_{12}$alkyl-substituted benzoyl; thienoyl or furoyl, $R_{10}$ is $C_1$–$C_{18}$alkylene, $C_4$–$C_{18}$alkylene which is interrupted by oxygen, sulfur or >N—R$_{11}$; $C_4$–$C_{18}$alkenylene, phenylethylene,

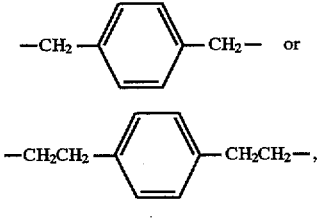

$R_{11}$ is hydrogen or $C_1$–$C_8$alkyl, $R_{12}$ and $R_{13}$, independently of one another, are hydrogen, CF$_3$, $C_1$–$C_{12}$alkyl or phenyl or $R_{12}$ and $R_{13}$, together with the carbon atom to which they are bonded, form an unsubstituted or $C_1$–$C_4$alkyl-substituted $C_5$–$C_8$cycloalkylidene ring;

X is a direct bond, oxygen, sulfur or

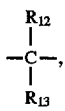

n is 1 or 2,
p is 0, 1 or 2,
q is an integer from 3 to 8, and
r is 1 or 2.

2. A compound according to claim 1, in which
$R_1$ and $R_2$, independently of one another, are hydrogen, $C_1$–$C_{18}$alkyl, $C_2$–$C_{18}$alkenyl, $C_5$–$C_8$cycloalkyl, unsubstituted or $C_1$–$C_4$alkyl-substituted phenyl, $C_5$–$C_8$cycloalkenyl, $C_7$–$C_9$phenylalkyl or —$CH_2$—S—$R_7$, $R_4$ is hydrogen, $C_1$–$C_{18}$alkyl, $C_2$–$C_{18}$alkenyl, $C_5$–$C_8$cycloalkyl, unsubstituted or $C_1$–$C_4$alkyl-substituted phenyl; $C_5$–$C_8$-cycloalkenyl, $C_7$–$C_9$-phenylalkyl, —$CH_2$—S—$R_7$, —$(CH_2)_p COOR_8$ or —$(CH_2)_q OR_9$, $R_5$ is hydrogen, $C_1$–$C_4$alkyl, OH, —$CH_2CN$, $C_4$–$C_{18}$alkoxy, $C_5$–$C_2$cycloalkoxy, allyl, propargyl, acetyl or $C_7$–$C_9$phenylalkyl; or $R_5$ furthermore is a radical of the formula II

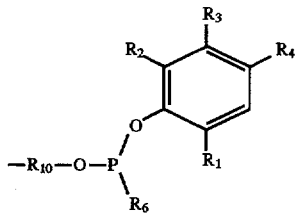

in which
$R_6$ is as defined below for n=1,
if n is 1, $R_6$ is $C_1$–$C_{18}$alkyl, $C_2$–$C_{18}$alkenyl, $C_5$–$C_8$cycloalkyl, unsubstituted or $C_1$–$C_4$alkyl- or phenyl-substituted phenyl; $C_5$–$C_8$cycloalkenyl or $C_7$–$C_9$phenylalkyl which is unsubstituted or substituted on the phenyl ring by 1 to 3 $C_1$–$C_4$alkyl;

$R_7$ is $C_1$–$C_{18}$alkyl, $C_5$–$C_{12}$cycloalkyl, unsubstituted or $C_1$–$C_4$alkyl-substituted phenyl; $C_7$–$C_9$phenylalkyl or —$(CH_2)_r COOR_8$, $R_8$ is $C_1 C_{18}$alkyl, $C_5$–$C_{12}$cycloalkyl, unsubstituted or $C_1$–$C_4$alkyl-substituted phenyl; or $C_7$–$C_9$phenylalkyl, $R_9$ is $C_1$–$C_{18}$alkyl, unsubstituted or $C_1$–$C_4$alkyl-substituted phenyl; $C_7$–$C_9$phenylalkyl, $C_1$–$C_{18}$alkanoyl, $C_3$–$C_{18}$alkenoyl, $C_2$–$C_{18}$alkanoyl which is interrupted by oxygen, sulfur or >N—$R_{11}$; $C_6$–$C_9$cycloalkylcarbonyl, or unsubstituted or $C_1$–$C_4$alkyl-substituted benzoyl, $R_{10}$ is $C_1$–$C_{12}$alkylene, $C_4$–$C_{12}$alkylene which is interrupted by oxygen, sulfur or >R—$R_{11}$; $C_4$–$C_8$alkenylene,

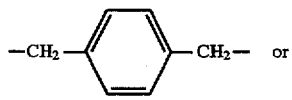

$R_{12}$ and $R_{13}$, independently of one another, are hydrogen, $CF_3$, $C_1$–$C_8$alkyl or phenyl, or $R_{12}$ and $R_{13}$, together with the carbon atom to which they are bonded, form a $C_5$–$C_8$cycloalkylidene ring.

3. A compound according to claim 1, in which $R_1$, $R_2$ and $R_4$, independently of one another, are hydrogen, $C_1$–$C_8$alkyl, cyclohexyl or phenyl.

4. A compound according to claim 1, in which
$R_5$ is hydrogen, $C_1$–$C_4$alkyl, $C_4$–$C_{16}$alkoxy, $C_5$–$C_8$cycloalkoxy, allyl, propargyl, acetyl, benzyl or a radical of the formula II

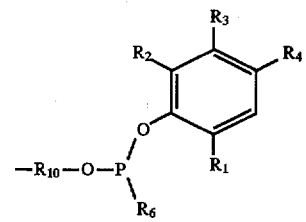

in which
$R_6$ is unsubstituted or $C_1$–$C_4$alkyl-substituted phenyl, and
$R_{10}$ is $C_1$–$C_4$alkylene.

5. A compound according to claim 1, in which
$R_1$ and $R_2$, independently of one another, are hydrogen, $C_1$–$C_{12}$alkyl, $C_2$–$C_{12}$alkenyl, cyclohexyl, phenyl, cyclohexenyl or benzyl, $R_4$ is hydrogen, $C_1$–$C_{12}$alkyl, $C_2$–$C_{12}$alkenyl, cyclohexyl, phenyl, cyclohexenyl, benzyl, —$CH_2$—S—$R_7$, —$(CH_2)_p COOR_8$ or —$(CH_2)_q OR_9$, $R_5$ is hydrogen, $C_1$–$C_4$alkyl, $C_4$–$C_{16}$alkoxy, $C_5$–$C_8$cycloalkoxy, allyl, propargyl, acetyl or benzyl; or $R_5$ furthermore is a radical of the formula II

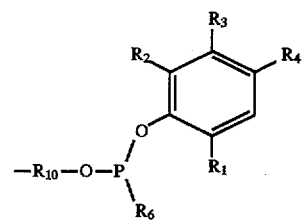

in which
$R_6$ is as defined below for n=1,
if n is 1, $R_6$ is $C_1$–$C_{12}$alkyl, $C_2$–$C_{12}$alkenyl, cyclohexyl, unsubstituted or $C_1$–$C_4$alkyl-substituted phenyl; cyclohexenyl or benzyl;

$R_7$ is $C_1$–$C_{12}$alkyl, $C_5$–$C_8$cycloalkyl, phenyl, benzyl or —$(CH_2)_r COOR_8$, $R_8$ is $C_1$–$C_{12}$alkyl, $C_5$–$C_8$cycloalkyl, phenyl or benzyl, $R_9$ is $C_1$–$C_{12}$alkyl, phenyl, benzyl, $C_1$–$C_{12}$alkanoyl, $C_2$–$C_{12}$alkanoyl which is interrupted by oxygen; cyclohexylcarbonyl or benzoyl, $R_{10}$ is $C_1$–$C_8$alkylene, $C_4$–$C_8$alkylene which is interrupted by oxygen, or $C_4$–$C_8$alkenylene, $R_{12}$ and $R_{13}$, independently of one another, are hydrogen, $CF_3$ or $C_1$–$C_4$alkyl, or $R_{12}$ and $R_{13}$, together with the carbon atom to which they are bonded, form a cyclohexylidene ring;

X is a direct bond, oxygen or

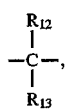

p is 2, q is an integer from 3 to 6, and r is 1.

6. A compound according to claim 1, in which $R_1$ and $R_2$, independently of one another, are hydrogen, $C_1$–$C_8$alkyl, cyclohexyl or phenyl, $R_4$ is hydrogen, $C_1$–$C_8$alkyl, cyclohexyl or —$(CH_2)_p$COOR$_8$, $R_5$ is hydrogen, $C_1$–$C_4$alkyl, $C_6$–$C_{12}$alkoxy, acetyl or benzyl; or $R_5$ furthermore is a radical of the formula II

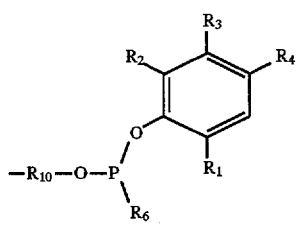

in which $R_6$ is as defined below for n=1, f n is 1, $R_6$ is $C_1$–$C_{12}$alkyl, cyclohexyl, phenyl or benzyl;

$R_8$ is $C_1$–$C_{12}$alkyl or benzyl, $R_{10}$ is $C_1$–$C_8$alkylene or $C_4$–$C_8$alkylene which is interrupted by oxygen, $R_{12}$ and $R_{13}$, independently of one another, are hydrogen or $C_1$–$C_4$alkyl, or $R_{12}$ and $R_{13}$, together with the carbon atom to which they are bonded, form a cyclohexylidene ring;

X is a direct bond or

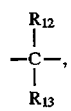

and p is 2.

7. A compound according to claim 1, in which $R_1$ and $R_2$, independently of one another, are $C_1$–$C_4$alkyl, $R_3$ is hydrogen, $R_4$ is $C_1$–$C_4$alkyl, $R_5$ is methyl or a radical of the formula II

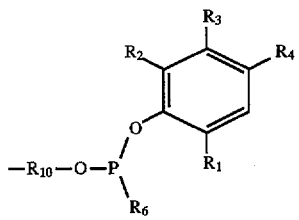

in which $R_6$ is as defined below for n=1, if n is 1, $R_6$ is phenyl, if n is 2, $R_6$ is a radical of the formula III

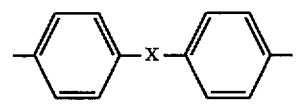

$R_{10}$ is ethylene,

X is a direct bond, and n is 1 or 2.

8. A composition comprising
 a) an organic material which is subjected to oxidative, thermal or light-induced degradation and
 b) at least one compound of the formula I according to claim 1.

9. A composition according to claim 8, additionally comprising further additives in addition to components (a) and (b).

10. A composition according to claim 9, wherein the further additives are phenolic antioxidants, light stabilizers and/or processing stabilizers.

11. A composition according to claim 9, wherein the further additive is at least one compound of the benzofuran-2-one type.

12. A composition according to claim 8, wherein component (a) is a natural, semisynthetic or synthetic polymer.

13. A composition according to claim 8, wherein component (a) is a thermoplastic polymer.

14. A composition according to claim 8, wherein component (a) is a polyolefin.

15. A composition according to claim 8, wherein component (a) is polyethylene or polypropylene.

16. A process for the stabilization of an organic material against oxidative, thermal or light-induced degradation, which comprises incorporating or applying at least one compound of the formula I defined in claim 1 into or to this material.

* * * * *